United States Patent
Ballesteros

(10) Patent No.: US 8,196,775 B1
(45) Date of Patent: Jun. 12, 2012

(54) GLOVE DISPENSER WITH GLOVE CATCH WELL

(76) Inventor: Fabian Alexander Ballesteros, Chino Hills, CA (US)

(*) Notice: Subject to any disclaimer, the term of this patent is extended or adjusted under 35 U.S.C. 154(b) by 647 days.

(21) Appl. No.: 12/257,890

(22) Filed: Oct. 24, 2008

(51) Int. Cl.
*A47K 10/24* (2006.01)

(52) U.S. Cl. .................. 221/309; 211/90.04; 211/85.17

(58) Field of Classification Search .................. 221/309; 211/90.04, 85.17
See application file for complete search history.

(56) References Cited

U.S. PATENT DOCUMENTS

| | | | | |
|---|---|---|---|---|
| 6,021,920 A * | 2/2000 | Aldape | | 221/96 |
| 6,062,421 A * | 5/2000 | Marley | | 221/45 |
| 7,246,710 B2 * | 7/2007 | Graneto, III | | 211/90.01 |
| 7,588,168 B2 * | 9/2009 | Bagwell et al. | | 221/96 |
| 2004/0099623 A1 * | 5/2004 | Kurtz et al. | | 211/85.17 |
| 2005/0087507 A1 * | 4/2005 | Graneto, III | | 211/71.01 |

* cited by examiner

*Primary Examiner* — Patrick Mackey
(74) *Attorney, Agent, or Firm* — Michael D. Eisenberg

(57) ABSTRACT

The present invention is directed toward a glove catch apparatus configured for connection to an existing glove dispenser. The glove catch apparatus comprises a frame, and access opening configured to permit access to a dispensing hole of the existing glove dispenser, and a well configured to catch dropped gloves dispensed from the glove dispenser. In addition, a glove dispenser, mountable to a wall, is disclosed. The glove dispenser comprises a well configured to catch dropped gloves dispensed from the glove dispenser.

11 Claims, 7 Drawing Sheets

GLOVE DISPENSER WITH GLOVE CATCH WELL

TECHNICAL FIELD

The present invention relates to a glove dispenser with a glove catch well, and more particularly, some embodiments relate to an apparatus for catching dropped gloves which is configured for connection to an existing glove dispenser.

BACKGROUND OF THE INVENTION

The subject invention generally relates to a glove dispenser with glove catch well. Disposable rubber gloves are used in a variety of different contexts including for example medical and healthcare, dental, laboratory, food service, automotive, and industrial environments. In the hospital environment, such gloves are medical safety accessories that ensure sanitary hospital conditions by limiting patients' exposure to infectious matter. They also serve to protect health professionals from disease through contact with bodily fluids.

Disposable gloves made of various materials, such as latex, vinyl or nitrile rubber, are widely available commercially. Such gloves generally are sold packaged tightly in a rectangular box with a tear away opening for accessing the gloves. The gloves are available in a variety of different sizes. Because of the widespread and varied uses for disposable gloves, there are a variety of glove dispensers commercially available which are configured to fit one or more boxes of disposable gloves. Some such existing glove dispensers are configured to be mounted on a wall.

In some environments, given that the gloves are packed tightly in the box, the gloves may at times stick together, and excess, trailing gloves fall to the ground. Such gloves become contaminated and unusable, and must generally be disposed of. Therefore, there is a need for a system that can prevent the unnecessary waste caused by gloves rendered unusable because they have fallen onto a contaminated floor, and the needless cost associated therewith. The glove catch apparatus disclosed in the present application can prevent such waste by allowing extra trailing gloves to fall inside a catch well, where the gloves can be retrieved for later use.

BRIEF SUMMARY OF EMBODIMENTS OF THE INVENTION

According to one embodiment of the invention, a glove catch apparatus is configured for connection to an existing glove dispenser. The glove catch apparatus comprises a frame, which itself comprises a front side and a back side, a top edge and a bottom edge. The glove catch further comprises an access opening configured to permit access to a dispensing hole of the existing glove dispenser when the glove catch apparatus is installed on the existing glove dispenser. In addition, the glove catch apparatus comprises a well configured to catch dropped gloves dispensed from the glove dispenser, the well connected to the front side of the frame and disposed below the access opening.

According to another embodiment of the invention, the glove catch apparatus comprises a plurality of access openings configured to permit access to a plurality of dispensing holes of the existing glove dispenser when the glove catch apparatus is installed on the existing glove dispenser. The glove catch apparatus further comprises a plurality of wells configured to catch dropped gloves dispensed from the glove dispenser, each well disposed below each of the plurality of access openings of the glove catch apparatus.

According to another embodiment of the invention, the frame of the glove catch apparatus comprises: a top connecting border connected to the top edge, for securing the glove catch apparatus to the existing glove dispenser; and a connecting side border for securing the glove catch apparatus to the existing glove dispenser. The connecting borders comprise a connection mechanism for securing the glove catch apparatus to the existing glove dispenser.

In a variant of the glove catch apparatus, the connection mechanism for securing the glove catch apparatus to the existing glove dispenser comprises through holes for securing the glove catch apparatus to the existing glove dispenser.

In a further variant of the invention, the glove catch apparatus further comprises a top flange configured to fit over a top of the existing glove dispenser for supporting the glove catch apparatus. The glove catch apparatus also comprises a bottom flange configured to fit over a bottom of the existing glove dispenser, the bottom flange connectable to the bottom of the existing glove dispenser.

In yet another variant of the glove catch apparatus disclosed herein, the well further comprises: left and right side walls connected to the front side of the frame and extending out from the frame; a front wall connected between the left and right side walls; and a bottom connected between the left and right side walls and connected between the front wall and the front side of the frame and extending out from the frame.

In one embodiment of the glove catch apparatus, the well further comprises a curved interior surface.

In another embodiment, the access opening is configured to fully envelope the dispensing hole.

In yet another embodiment, the glove catch apparatus further comprises a hook member connected to the flange, wherein the hook member comprises a lip member extending from the flange and configured to hook over the existing glove dispenser.

According to yet a further embodiment of the invention, the glove catch apparatus comprises a plurality of access openings configured to permit access to a plurality of dispensing holes of the existing glove dispenser when the glove catch apparatus is installed on the existing glove dispenser. The glove catch apparatus further comprises a plurality of wells configured to catch dropped gloves dispensed form the glove dispenser, each well disposed below each of the plurality of access openings of the existing glove dispenser.

In one variant of the invention, a glove dispenser, mountable to a wall, is disclosed. The glove dispenser comprises: a front frame, itself comprising a front side and a back side, a top edge and a bottom edge; an access opening configured to permit access to a removable container of gloves; a well configured to catch dropped gloves dispensed from the glove dispenser, the well connected to the front side of the frame and disposed below the access opening and above the bottom edge; and a platform connected to the back side of the front frame and disposed below the access opening, configured to support the removable container of gloves against the access opening for dispensing gloves from the container of gloves through the access opening.

In another variant, the glove dispenser further comprises a rear frame connected to the platform opposite the front frame. The rear frame is configured for securing the glove dispenser to the wall.

In yet another variant, the glove dispenser further comprises a top frame connected to the top edge of the front frame and also connected to a top edge of the rear frame. The glove dispenser also comprises a bottom frame connected to the bottom edge of the front frame and also connected to a bottom edge of the rear frame.

In yet a further variant of the invention, the glove dispenser further comprises a side frame connected to the rear frame and also connected to a side edge of the front frame. A side opposite the side frame comprises an opening for placement of the removable container of gloves into the glove dispenser.

In another embodiment of the glove dispenser, the well further comprises left and right side walls connected to the front side of the front frame and extending out from the front frame, and a front wall connected between the left and right side walls. In addition, the well comprises a bottom connected between the left and right side walls and connected between the front wall and the front side of the front frame and extending out from the front frame.

In yet another embodiment, the well further comprises a curved interior surface.

In yet a further embodiment of the invention, the glove dispenser comprises a plurality of access openings configured to permit access to a plurality of removable containers of gloves. The glove dispenser further comprises a plurality of wells configured to catch dropped gloves dispensed from the glove dispenser, the plurality of wells connected to the front side of the frame. Each of the plurality of wells is disposed below each of the plurality of access openings. In addition, the glove dispenser comprises a plurality of platforms connected to the back side of the front frame. Each of the plurality of platforms is disposed below each of the plurality of access openings. The plurality of platforms are configured to support the plurality of removable containers of gloves against each of the plurality of access openings for dispensing gloves from the containers of gloves through the access openings.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
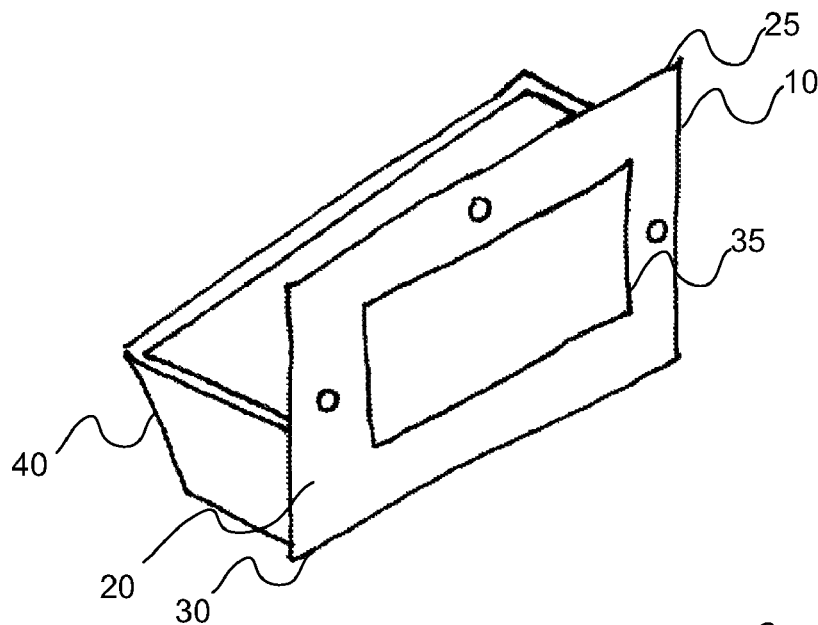
FIG. 1 is a perspective view of an embodiment of the glove catch apparatus configured for connection to an existing glove dispenser.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention is directed toward a glove dispenser with glove catch well. According to one embodiment of the invention, referring to FIGS. 1-4, a glove catch apparatus is configured for connection to an existing glove dispenser. The existing glove dispenser may be of the variety that is configured to be mounted on a wall. The glove catch apparatus comprises a frame 10, which itself comprises a front side 15 and a back side 20, a top edge 25 and a bottom edge 30. The glove catch further comprises an access opening 35 configured to permit access to a dispensing hole of the existing glove dispenser when the glove catch apparatus is installed on the existing glove dispenser. In addition, the glove catch apparatus comprises a well 40 configured to catch dropped gloves dispensed from the glove dispenser, the well 40 connected to the front side 15 of the frame and disposed below the access opening 35.

Figure 2:
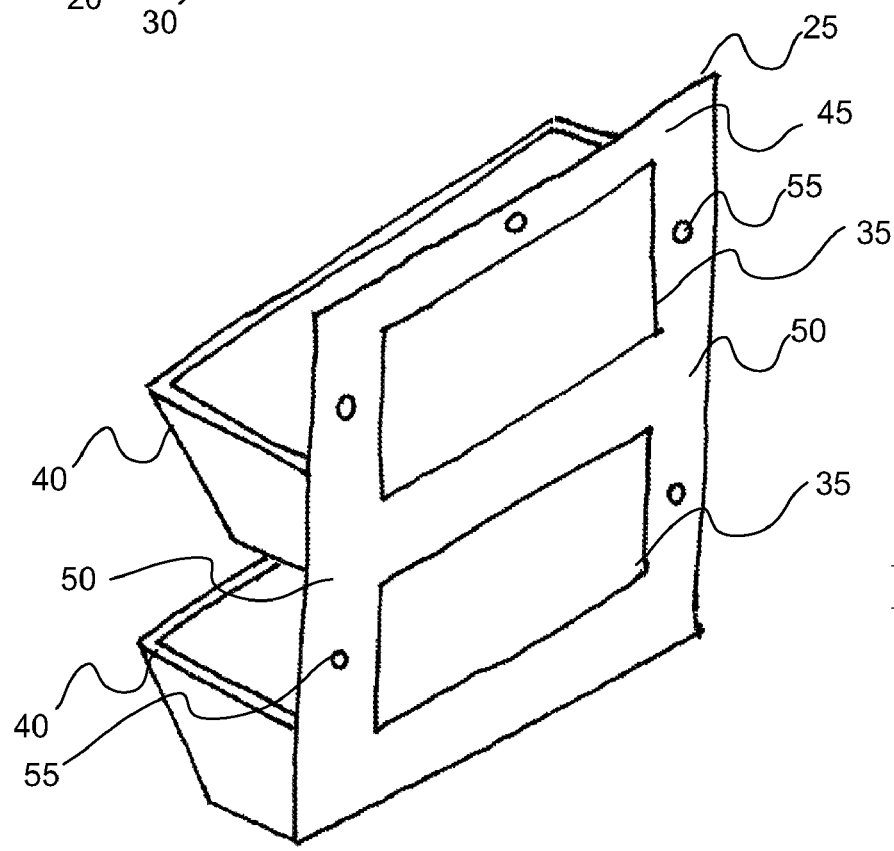
FIG. 2 is a perspective view of an embodiment of the glove catch apparatus configured for connection to an existing glove dispenser, wherein the existing glove dispenser dispenses gloves from two separate containers of gloves.
Figure 3:
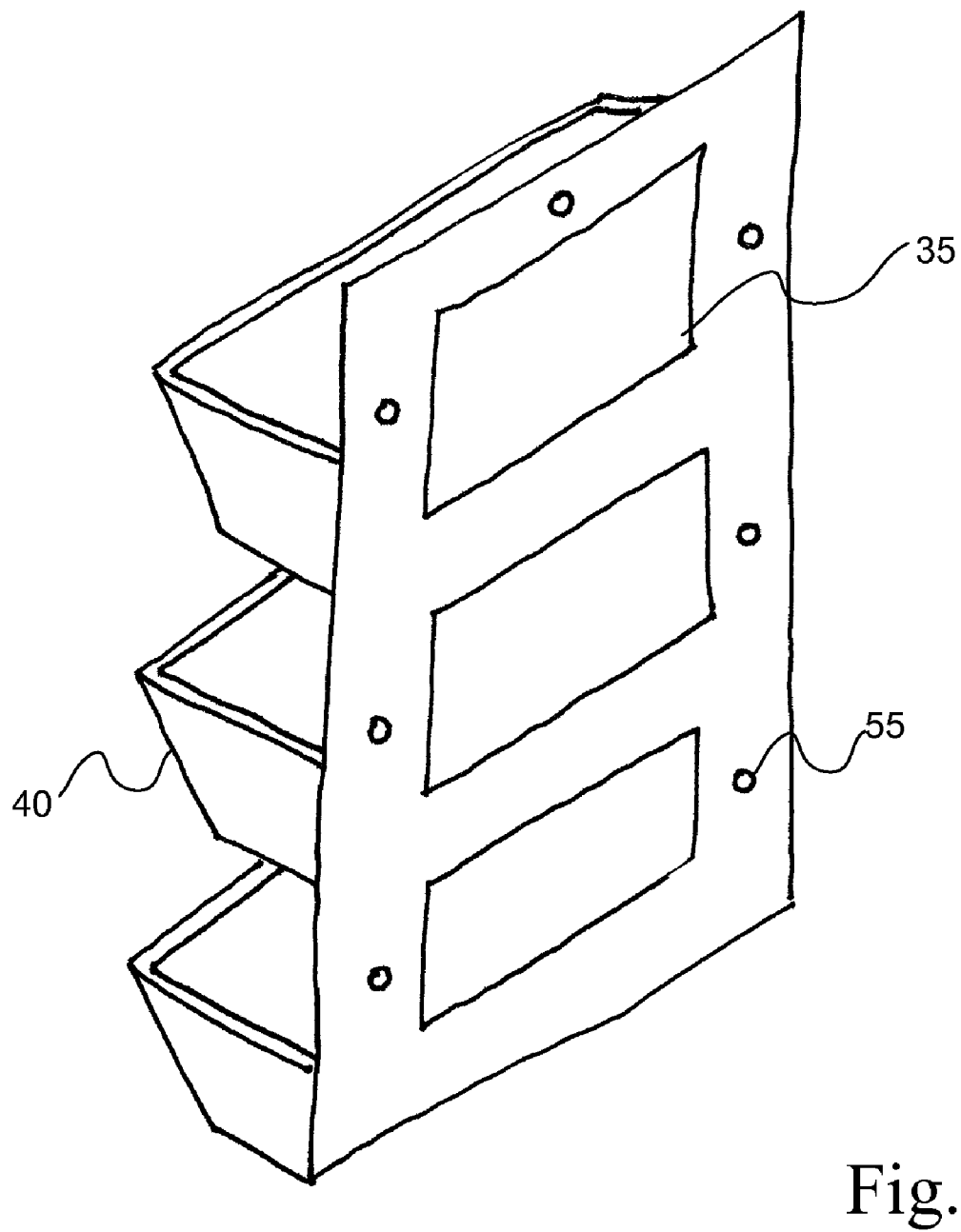
FIG. 3 is a perspective view of an embodiment of the glove catch apparatus configured for connection to an existing glove dispenser, wherein the existing glove dispenser dispenses gloves from three separate containers of gloves.
Figure 5:
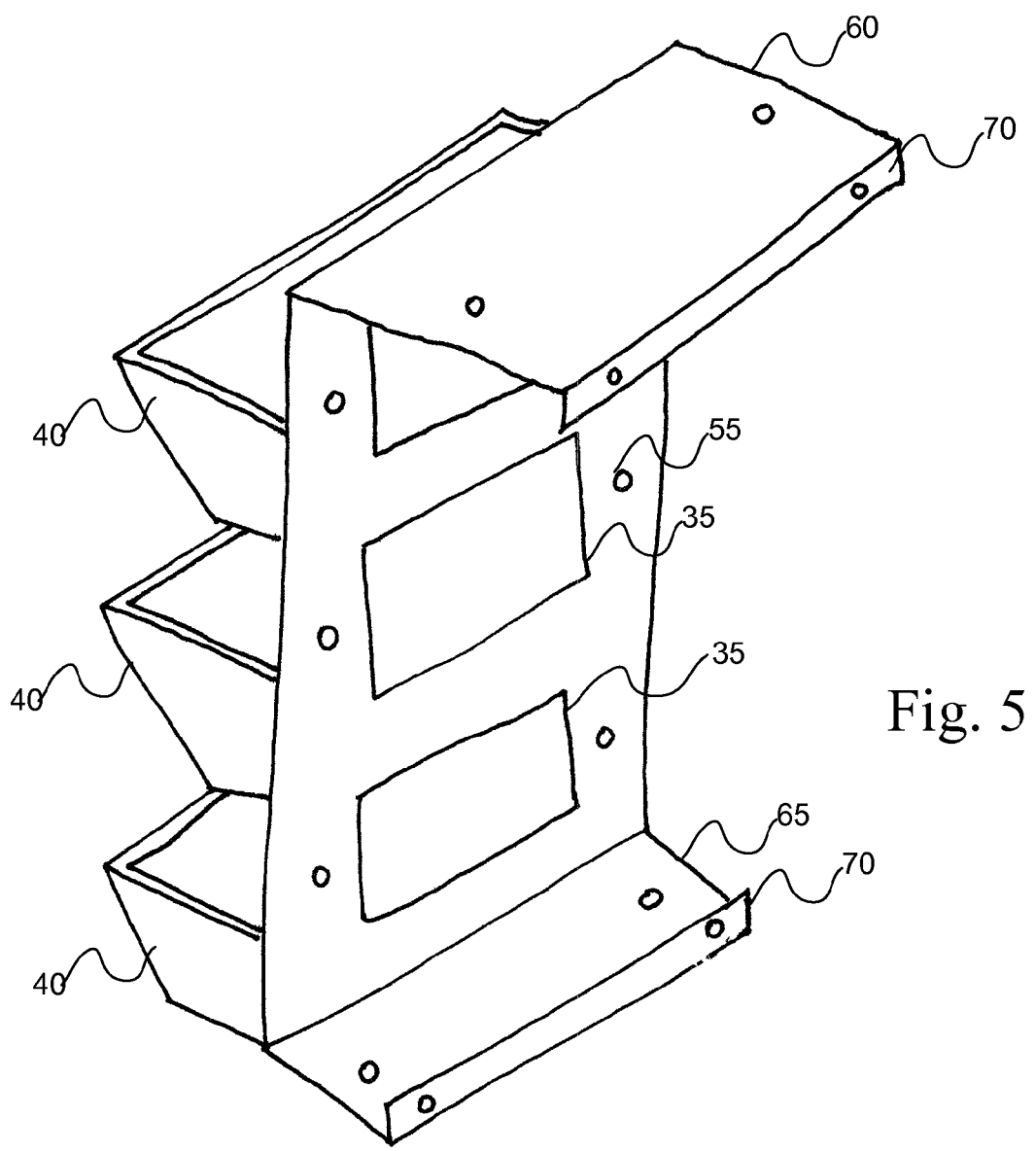
FIG. 5 is a perspective view of an embodiment of the glove catch apparatus configured for connection to an existing glove dispenser, wherein the glove catch apparatus has a top flange and a bottom flange.

According to another embodiment of the invention, referring to FIGS. 2-3, and FIG. 5, the glove catch apparatus comprises a plurality of access openings 35 configured to permit access to a plurality of dispensing holes of the existing glove dispenser when the glove catch apparatus is installed on the existing glove dispenser. The glove catch apparatus further comprises a plurality of wells 40 configured to catch dropped gloves dispensed from the glove dispenser, each well 40 disposed below each of the plurality of access openings 35 of the glove catch apparatus.

According to yet another embodiment of the invention, referring to FIGS. 1-5, the frame 10 of the glove catch apparatus comprises: a top connecting border 45 connected to the top edge 25, for securing the glove catch apparatus to the existing glove dispenser; and a connecting side border 50 for securing the glove catch apparatus to the existing glove dispenser. The connecting borders comprise a connection mechanism for securing the glove catch apparatus to the existing glove dispenser.

In a variant of the glove catch apparatus, the connection mechanism for securing the glove catch apparatus to the existing glove dispenser comprises through holes 55 for securing the glove catch apparatus to the existing glove dispenser.

In a further variant of the invention, referring to FIG. 5, the glove catch apparatus further comprises a top flange 60 configured to fit over a top of the existing glove dispenser for supporting the glove catch apparatus. The glove catch apparatus also comprises a bottom flange 65 configured to fit over a bottom of the existing glove dispenser, the bottom flange connectable to the bottom of the existing glove dispenser.

Figure 4:
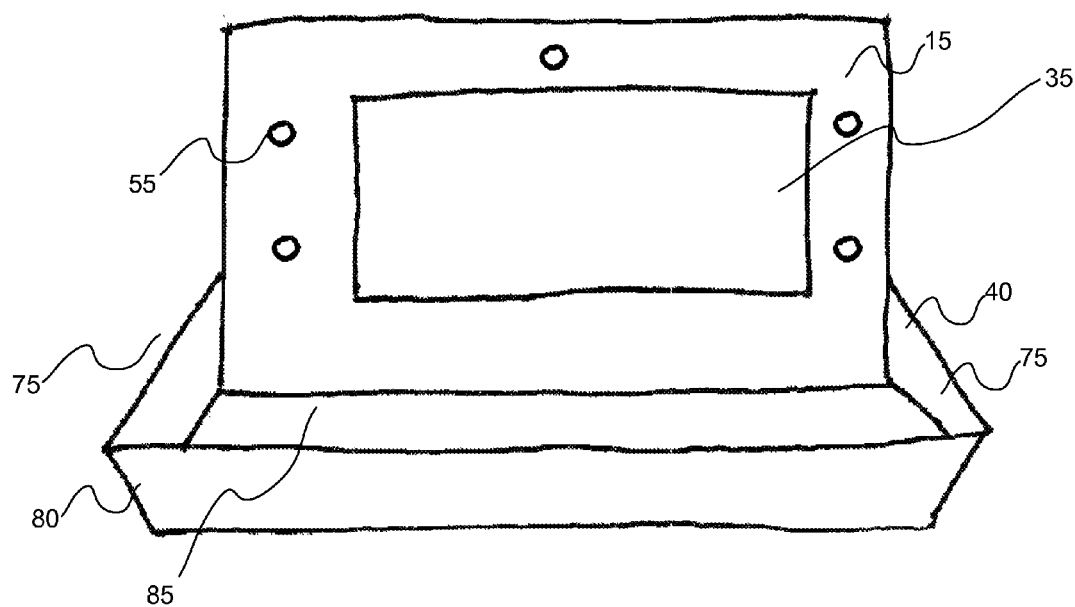
FIG. 4 is a front view of an embodiment of the glove catch apparatus configured for connection to an existing glove dispenser, wherein the existing glove dispenser dispenses gloves from a single container of gloves.

In yet another variant of the glove catch apparatus disclosed herein, referring to FIG. 4, the well further comprises: left and right side walls 75 connected to the front side 15 of the frame and extending out from the frame; a front wall 80 connected between the left and right side walls; and a bottom 85 connected between the left and right side walls 75 and connected between the front wall 80 and the front side 15 of the frame and extending out from the frame. In another variant, the front wall 80 has a notched opening emanating from a top edge of the front wall 80, which opening facilitates removal of gloves from the access opening, by creating additional clearance for the user's hand. The notched opening may be curved, as in a semi-circle, or angular, as in a rectangular cutout.

In one embodiment of the glove catch apparatus, the well 40 further comprises a curved interior surface.

In another embodiment, the access opening 35 is configured to fully envelope the dispensing hole.

In yet another embodiment, the glove catch apparatus further comprises a hook member 70 connected to the flange 60, 65, wherein the hook member 70 comprises a lip member extending from the flange and configured to hook over the existing glove dispenser.

According to yet a further embodiment of the invention, referring to FIG. 5, the glove catch apparatus comprises a plurality of access openings 35 configured to permit access to a plurality of dispensing holes of the existing glove dispenser when the glove catch apparatus is installed on the existing glove dispenser. The glove catch apparatus further comprises a plurality of wells 40 configured to catch dropped gloves dispensed form the glove dispenser, each well disposed below each of the plurality of access openings 35.

Figure 6:
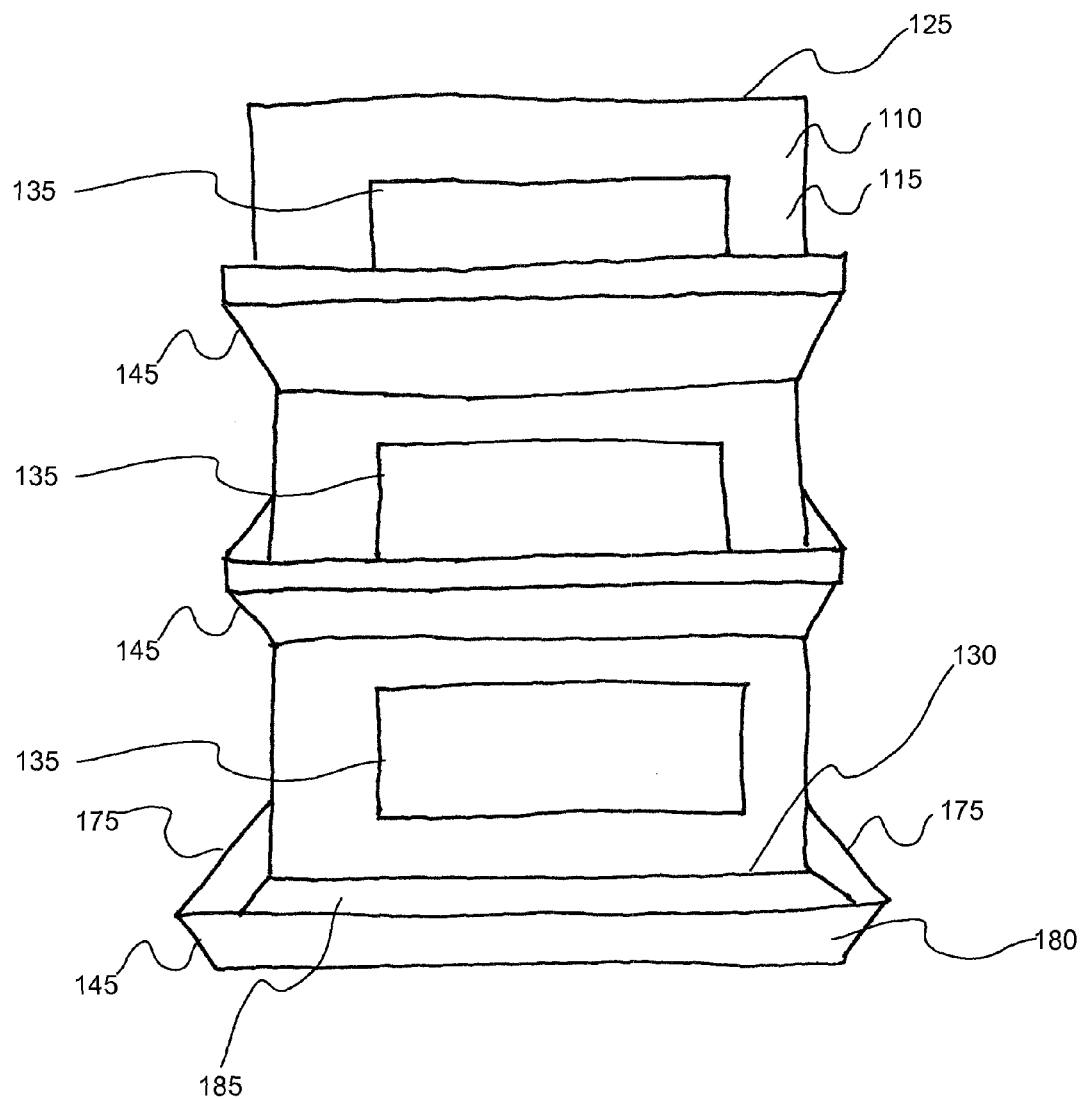
FIG. 6 is a front view of a preferred embodiment of the glove dispenser with glove catch well, in which the dispenser is configured to dispense gloves from three separate containers of gloves.
Figure 7:
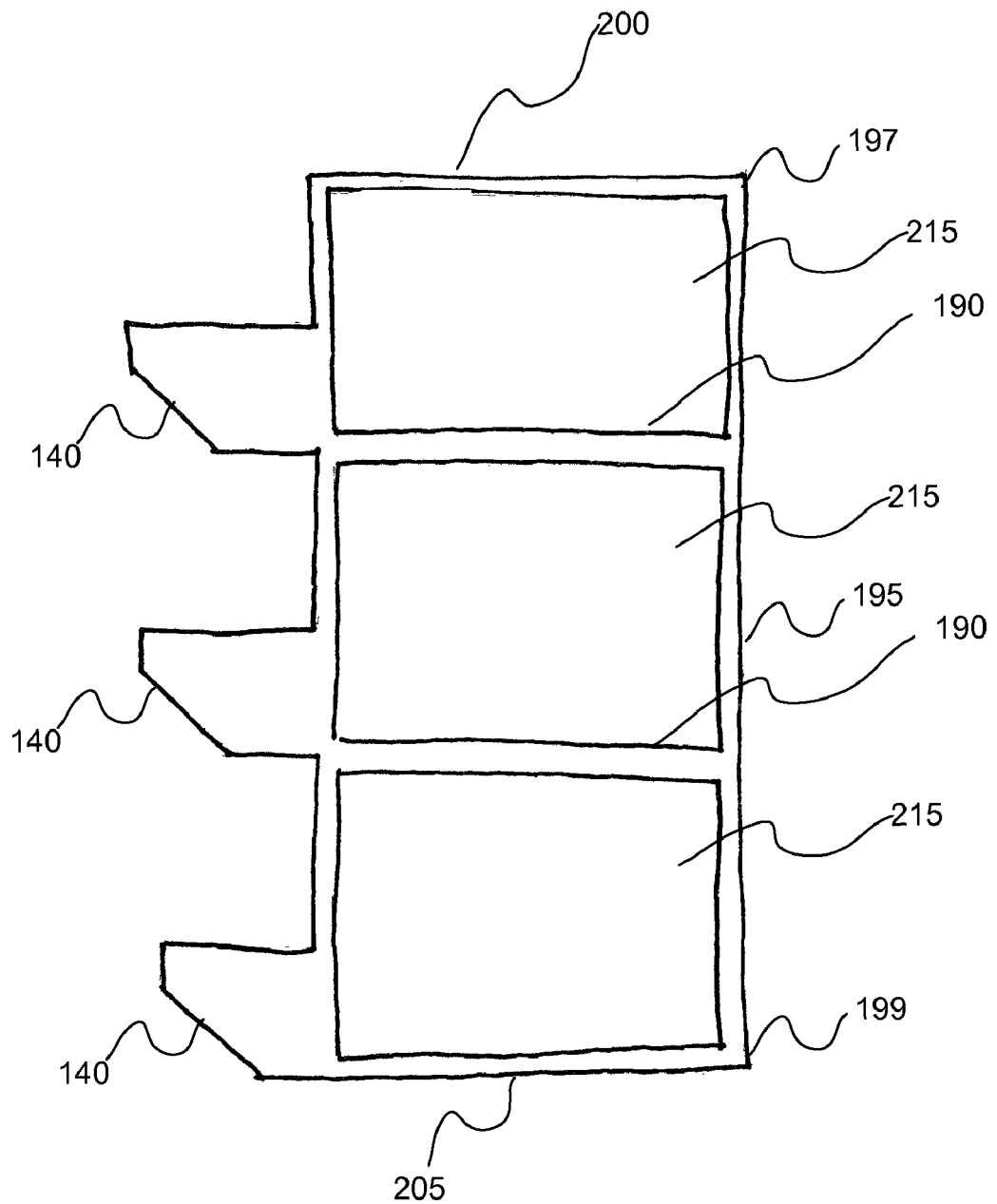
FIG. 7 is a side view of a preferred embodiment of the glove dispenser with glove catch well, in which the dispenser is configured to dispense gloves from three separate containers of gloves.
Figure 8:
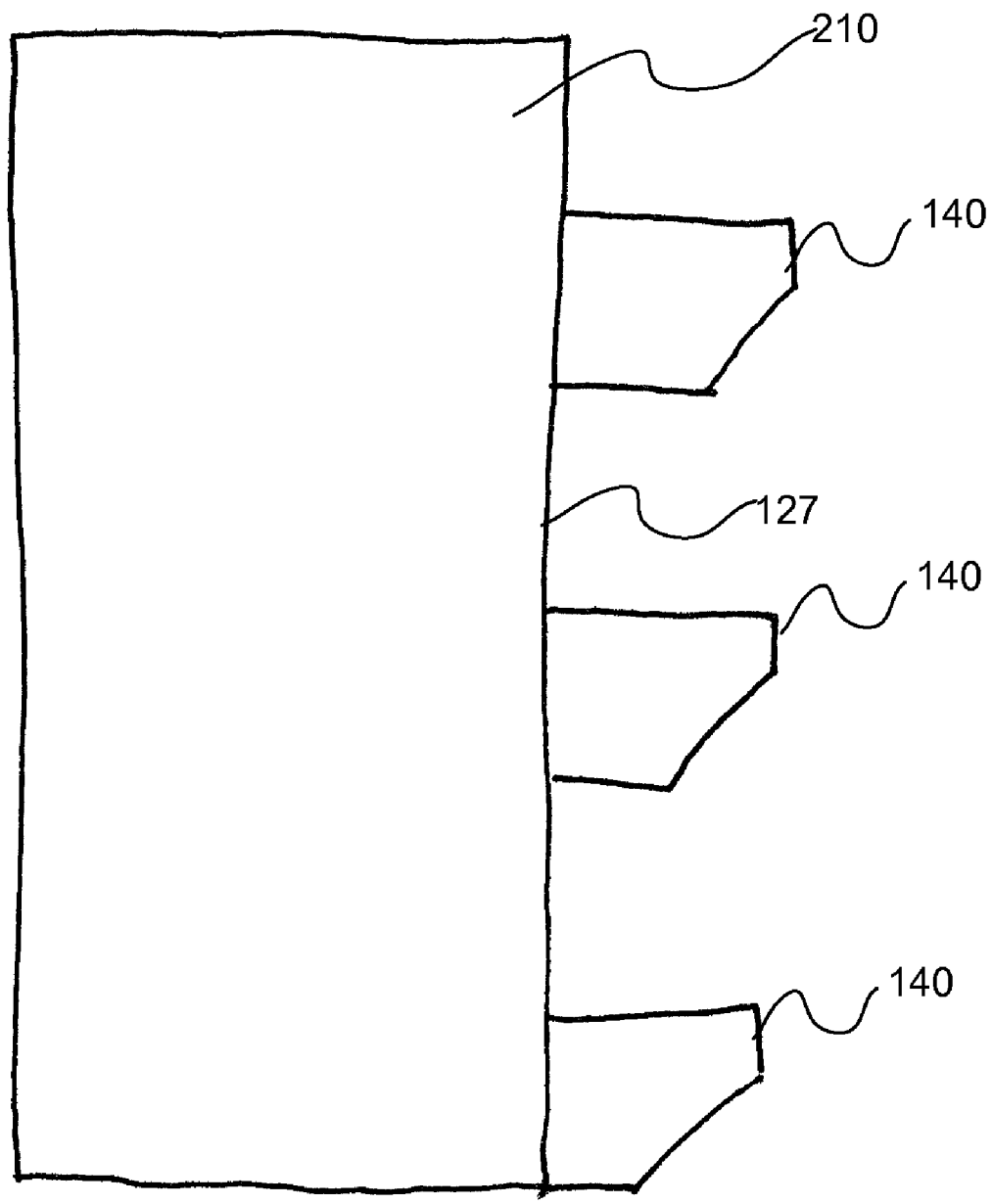
FIG. 8 is an opposite side view of a preferred embodiment of the glove dispenser with glove catch well, in which the dispenser is configured to dispense gloves from three separate containers of gloves.

In one variant of the invention, referring to FIGS. 6-8, a glove dispenser, mountable to a wall, is disclosed. The glove dispenser comprises: a front frame 110, itself comprising a front side 115 and a back side, a top edge 125 and a bottom edge 130; an access opening 135 configured to permit access to a removable container of gloves; and a well 140 configured to catch dropped gloves dispensed from the glove dispenser. The well 140 itself is connected to the front side 115 of the frame 110 and disposed below the access opening 135. In addition, the glove dispenser comprises a platform 190 connected to the back side of the front frame 110 and disposed below the access opening 135, configured to support the removable container of gloves against the access opening 135 for dispensing gloves from the container of gloves through the access opening 135.

In another variant, referring to FIGS. 7-8, the glove dispenser further comprises a rear frame 195 connected to the platform 190 opposite the front frame 110. The rear frame 195 is configured for securing the glove dispenser to the wall.

In yet another variant, referring to FIGS. 7-8, the glove dispenser further comprises a top frame 200 connected to the top edge 125 of the front frame 110 and also connected to a top edge 197 of the rear frame 195. The glove dispenser also comprises a bottom frame 205 connected to the bottom edge 130 of the front frame 110 and also connected to a bottom edge 199 of the rear frame 195.

In yet a further variant of the invention, the glove dispenser further comprises a side frame 210 connected to the rear frame 195 and also connected to a side edge 127 of the front frame 110. A side 215 opposite the side frame 210 comprises an opening for placement of the removable container of gloves into the glove dispenser.

In another embodiment of the glove dispenser, referring to FIG. 6, the well 140 further comprises left and right side walls 175 connected to the front side 115 of the front frame and extending out from the front frame 110, and a front wall 180 connected between the left and right side walls 175. In addition, the well comprises a bottom 185 connected between the left and right side walls 175 and connected between the front wall 180 and the front side 115 of the front frame 110 and extending out from the front frame 110.

In yet another embodiment, the well 140 further comprises a curved interior surface.

In yet a further embodiment of the invention, the glove dispenser comprises a plurality of access openings configured to permit access to a plurality of removable containers of gloves. The glove dispenser further comprises a plurality of wells configured to catch dropped gloves dispensed from the glove dispenser, the plurality of wells connected to the front side of the frame. Each of the plurality of wells is disposed below each of the plurality of access openings. In addition, the glove dispenser comprises a plurality of platforms connected to the back side of the front frame. Each of the plurality of platforms is disposed below each of the plurality of access openings. The plurality of platforms are configured to support the plurality of removable containers of gloves against each of the plurality of access openings for dispensing gloves from the containers of gloves through the access openings.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A glove catch apparatus configured for connection to an existing glove dispenser mounted on a wall, comprising:
   a frame attachable to the existing glove dispenser mounted on a wall, comprising:
      a front side and a back side, a top edge and a bottom edge;
      a top connecting border connected to the top edge, for securing the glove catch apparatus to the existing glove dispenser; and
      a connecting side border for securing the glove catch apparatus to the existing glove dispenser;
      wherein the connecting borders comprise a connection mechanism for securing the glove catch apparatus to the existing glove dispenser;
   an access opening configured to permit access to a dispensing hole of the existing glove dispenser when the glove catch apparatus is installed on the existing glove dispenser, the access opening is configured to fully envelope the dispensing hole; and
   a top flange configured to fit over a top of the existing glove dispenser for supporting the glove catch apparatus; and
   a bottom flange configured to fit over a bottom of the existing glove dispenser, the bottom flange connectable to the bottom of the existing glove dispenser;
   a well configured to catch dropped gloves dispensed from the glove dispenser, the well connected to the front side of the frame and disposed below the access opening, the well comprising:
      left and right side walls connected to the front side of the frame and extending out from the frame;
      a front wall connected between the left and right side walls; and
      a bottom connected between the left and right side walls and connected between the front wall and the front side of the frame and extending out from the frame;
   a hook member connected to at least one of the top flange or bottom flange, wherein the hook member comprises a lip member extending from the flange and configured to hook over the existing glove dispenser;
   wherein the glove catch apparatus is operable to attach to the existing glove dispenser via attachment to the frame.

2. The glove catch apparatus of claim 1, further comprising:
   a plurality of access openings configured to permit access to a plurality of dispensing holes of the existing glove dispenser when the glove catch apparatus is installed on the existing glove dispenser; and
   a plurality of wells configured to catch dropped gloves dispensed form the glove dispenser, each well disposed below each of the plurality of access openings of the existing glove dispenser.

3. A glove dispenser, mountable to a wall, comprising:
   a front frame, comprising a front side and a back side, a top edge and a bottom edge, and left and right sides;
   an access opening located on at least one of the sides configured to permit access to a removable container of gloves;
   a well configured to catch dropped gloves dispensed from the glove dispenser, the well connected to the front side of the frame and disposed below the access opening and above the bottom edge; and
   a platform connected to the back side of the front frame and disposed below the access opening, configured to support the removable container of gloves against the access opening for dispensing gloves from the container of gloves through the access opening.

4. The glove dispenser of claim 3, further comprising:
a rear frame connected to the platform opposite the front frame, the rear frame configured for securing the glove dispenser to the wall;
a top frame connected to the top edge of the front frame and also connected to a top edge of the rear frame; and
a bottom frame connected to the bottom edge of the front frame and also connected to a bottom edge of the rear frame;
a side frame connected to the rear frame and also connected to a side edge of the front frame, wherein a side opposite the side frame comprises an opening for placement of the removable container of gloves into the glove dispenser;
wherein the well further comprises:
  left and right side walls connected to the front side of the front frame and extending out from the front frame;
  a front wall connected between the left and right side walls; and
  a bottom connected between the left and right side walls and connected between the front wall and the front side of the front frame and extending out from the front frame.

5. The glove dispenser of claim 3, further comprising:
a plurality of access openings as recited in claim 3 configured to permit access to a plurality of removable containers of gloves;
a plurality of wells as recited in claim 3 configured to catch dropped gloves dispensed from the glove dispenser, the plurality of wells connected to the front side of the frame, wherein each of the plurality of wells is disposed below each of the plurality of access openings; and
a plurality of platforms as recited in claim 3 connected to the back side of the front frame, wherein each of the plurality of platforms is disposed below each of the plurality of access openings, and wherein the plurality of platforms are configured to support the plurality of removable containers of gloves against each of the plurality of access openings for dispensing gloves from the containers of gloves through the access openings.

6. A glove catch apparatus configured for connection to an existing glove dispenser, comprising:
a frame, comprising:
  a front side and a back side;
  a top edge and a bottom edge;
  a top connecting border connected to the top edge, for securing the glove catch apparatus to the existing glove dispenser; and
  a connecting side border for securing the glove catch apparatus to the existing glove dispenser;
  wherein the connecting borders comprise through holes for securing the glove catch apparatus to the existing glove dispenser;
an access opening configured to permit access to a dispensing hole of the existing glove dispenser when the glove catch apparatus is installed on the existing glove dispenser; and
a well configured to catch dropped gloves dispensed from the glove dispenser, the well connected to the front side of the frame and disposed below the access opening.

7. The glove catch apparatus of claim 6, further comprising:
a top flange configured to fit over a top of the existing glove dispenser for supporting the glove catch apparatus; and
a bottom flange configured to fit over a bottom of the existing glove dispenser, the bottom flange connectable to the bottom of the existing glove dispenser.

8. The glove catch apparatus of claim 6, wherein the well further comprises:
left and right side walls connected to the front side of the frame and extending out from the frame;
a front wall connected between the left and right side walls; and
a bottom connected between the left and right side walls and connected between the front wall and the front side of the frame and extending out from the frame.

9. The glove catch apparatus of claim 6, wherein the access opening is configured to fully envelope the dispensing hole.

10. The glove catch apparatus of claim 6, further comprising a hook member connected to at least one of the top flange or bottom flange, wherein the hook member comprises a lip member extending from the flange and configured to hook over the existing glove dispenser.

11. The glove catch apparatus of claim 6, further comprising:
a plurality of access openings as recited in claim 6 configured to permit access to a plurality of dispensing holes as recited in claim 6 of the existing glove dispenser when the glove catch apparatus is installed on the existing glove dispenser; and
a plurality of wells as recited in claim 6 configured to catch dropped gloves dispensed form the glove dispenser, each well disposed below each of the plurality of access openings of the existing glove dispenser.

* * * * *